(12) United States Patent
Van Camp et al.

(10) Patent No.: US 10,175,152 B2
(45) Date of Patent: Jan. 8, 2019

(54) DETERMINING AEROSOL MATERIAL COMPATIBILITY

(71) Applicant: The Boeing Company, Chicago, IL (US)

(72) Inventors: Conor J. Van Camp, Long Beach, CA (US); Chris T. Zervas, Yarrow Point, WA (US); Shawn H. Park, Cerritos, CA (US)

(73) Assignee: The Boeing Company, Chicago, IL (US)

( * ) Notice: Subject to any disclaimer, the term of this patent is extended or adjusted under 35 U.S.C. 154(b) by 123 days.

(21) Appl. No.: 15/375,243

(22) Filed: Dec. 12, 2016

(65) Prior Publication Data

US 2017/0089812 A1 Mar. 30, 2017

Related U.S. Application Data

(63) Continuation of application No. 14/447,554, filed on Jul. 30, 2014, now Pat. No. 9,546,933.

(51) Int. Cl.
*G01N 31/22* (2006.01)
*G01N 17/00* (2006.01)
(Continued)

(52) U.S. Cl.
CPC .................. *G01N 1/30* (2013.01); *A61L 9/14* (2013.01); *G01N 1/28* (2013.01); *G01N 1/31* (2013.01);
(Continued)

(58) Field of Classification Search
CPC .... A61L 9/14; A61L 2202/20; A61L 2202/25; A61L 2209/211; A61L 2/28; A61L 9/01; C12Q 1/22; G01N 17/00; G01N 31/226
See application file for complete search history.

(56) References Cited

U.S. PATENT DOCUMENTS 3,439,531 A 4/1969 Sipes
3,510,343 A 5/1970 Twells
(Continued)

OTHER PUBLICATIONS

"U.S. Appl. No. 14/447,554, Non Final Office Action dated Jun. 2, 2016", 12 pages.
(Continued)

*Primary Examiner* — David A Rogers
(74) *Attorney, Agent, or Firm* — Kwan & Olynick LLP

(57) ABSTRACT

Provided are methods for testing aerosol material compatibility of various samples to disinfectants, decontaminates, and other such materials that are used as aerosols. A test is performed in a controlled environment, such as an aerosol chamber, using a specific set of test parameters representative of actual use of tested materials, such as dispensing parameters and exposure parameters. During the test, a test surface of the sample is exposed to an aerosol mist. Other surfaces may be protected. After exposure to the aerosol mist, the sample may be allowed to sit for a period of time. The sample is later cleaned and tested to determine effects of various materials in the mist on the sample. In some embodiments, some or all operations may be repeated for the same sample or different samples. The test parameters may be varied to determine compatibility limits.

20 Claims, 4 Drawing Sheets

(51) Int. Cl.
 *G01N 1/30* (2006.01)
 *G01N 1/31* (2006.01)
 *G01N 1/34* (2006.01)
 *A61L 9/14* (2006.01)
 *G01N 1/28* (2006.01)
 *G01N 33/36* (2006.01)

(52) U.S. Cl.
 CPC .............. *G01N 1/34* (2013.01); *G01N 17/00* (2013.01); *G01N 17/002* (2013.01); *G01N 31/226* (2013.01); *G01N 33/367* (2013.01); *G01N 2001/317* (2013.01)

(56) References Cited

U.S. PATENT DOCUMENTS

| | | | |
|---|---|---|---|
| 4,585,571 A | 4/1986 | Bloom | |
| 4,759,867 A | 7/1988 | Choy et al. | |
| 6,046,150 A | 4/2000 | Choy et al. | |
| 6,074,741 A | 6/2000 | Murata et al. | |
| 6,756,352 B2 | 6/2004 | Makansi | |
| 8,394,253 B2 | 3/2013 | Peters et al. | |
| 8,794,546 B2 * | 8/2014 | Eley | B05B 1/12 239/438 |
| 9,185,908 B2 | 11/2015 | Krug et al. | |
| 9,226,495 B2 | 1/2016 | Berentsveig et al. | |
| 9,546,933 B2 | 1/2017 | Van Camp et al. | |
| 2003/0158459 A1 | 8/2003 | Tucker | |
| 2010/0173011 A1 | 7/2010 | Peters et al. | |
| 2010/0240799 A1 | 9/2010 | Hofmann et al. | |
| 2010/0294166 A1 | 11/2010 | Arafat | |
| 2010/0330196 A1 | 12/2010 | Ramirez et al. | |
| 2011/0200829 A1 | 8/2011 | Ober et al. | |
| 2011/0230474 A1 | 9/2011 | Grigorian et al. | |
| 2011/0271873 A1 | 11/2011 | Ohlhausen et al. | |
| 2012/0071438 A1 | 3/2012 | Pedersen et al. | |
| 2012/0121731 A1 | 5/2012 | Peters et al. | |
| 2012/0152148 A1 | 6/2012 | Dilley et al. | |
| 2012/0177746 A1 | 7/2012 | Ramirez et al. | |
| 2012/0199119 A1 | 8/2012 | Pardonge | |
| 2012/0208958 A1 | 8/2012 | Jahns et al. | |
| 2012/0263800 A1 | 10/2012 | Berentsveig et al. | |
| 2013/0085137 A1 | 4/2013 | Grigorian et al. | |
| 2013/0150313 A1 | 6/2013 | Flury et al. | |
| 2013/0181013 A1 | 7/2013 | Tasz et al. | |
| 2013/0233346 A1 | 9/2013 | Rochon et al. | |
| 2014/0030305 A1 * | 1/2014 | Krug | A01N 31/02 424/411 |
| 2014/0154670 A1 | 6/2014 | Williams, Jr. et al. | |
| 2016/0033374 A1 | 2/2016 | Van Camp et al. | |

OTHER PUBLICATIONS

"U.S. Appl. No. 14/447,554, Notice of Allowance dated Sep. 16, 2016", 5 pages.
"Standard Practice for Modified Salt Spray (Fog) Testing", ASTM International G85-11, 2011, 14 pages.
"Standard Practice for Operating Salt Spray (Fog) Apparatus", ASTM International B117-11, 2011, 12 pages.
"Standard Test Method for Delivery Rate of Aerosol Products", ASTM International D3069, 2013, 2 pages.
"Standard Test Method for Using Aerosol Filtration for Measuring the Performance of Porous Packaging Materials as a Surrogate Microbial Barrier", ASTM International F2638, 2012, 17 pages.

* cited by examiner

FIG. 1

DETERMINING AEROSOL MATERIAL COMPATIBILITY

CROSS-REFERENCE TO RELATED APPLICATIONS

This application is a continuation of U.S. application Ser. No. 14/447,554, entitled "DETERMINING AEROSOL MATERIAL COMPATIBILITY," filed on Jul. 30, 2014, which is incorporated herein by reference in its entirety for all purposes.

BACKGROUND

Bacterial and microbial contamination of confined spaces, such as aircraft cabins, has long been a major concern and source of infection. In some situations, many people share the same limited space for prolonged periods of time (e.g., during a flight) and may cause contamination and/or be exposed to various contaminants in that space. Bacteria, viruses, spores, and other disease-causing contaminants may adhere to surfaces and/or linger in the air after being discharged by disease carrying humans (e.g., coughing, sneezing, touching surfaces) and/or after being maliciously introduced into the space (e.g., during a biological attack). Diseases spread by such contaminants include, but are not limited to, common cold, influenza, rotavirus, hepatitis A, tuberculosis, conjunctivitis, staphylococcal bacterial infections, and strep throat. Decontamination can be difficult because of vast surfaces being potentially contaminated. Often contaminated surfaces are hidden or not directly accessible for cleaning. Aerosolized decontaminates, disinfectants, and other such chemicals have been recently proposed for various applications, such as decontamination of aircraft cabins. However, applying these chemicals may damage these surfaces. Yet methods for testing material compatibility with aerosolized chemicals are not available.

SUMMARY

Provided are methods for testing aerosol material compatibility of various samples to disinfectants, decontaminates, and other such materials that are used as aerosols. A test is performed in a controlled environment, such as an aerosol chamber, using a specific set of test parameters representative of actual use of tested materials, such as dispensing parameters and exposure parameters. During the test, a test surface of a sample is exposed an aerosol mist. Other surfaces may be protected. After exposure to the aerosol mist, the sample may be allowed to sit for a period of time. The sample is later cleaned and tested to determine effects of various materials in the mist on the sample. In some embodiments, some or all operations may be repeated for the same sample or different samples. The test parameters may be varied to determine compatibility limits.

In some embodiments, a method for testing aerosol material compatibility involves dispensing a first aerosol mist onto the test surface of a first sample using a first set of test parameters. The first aerosol mist comprises at least one of a first disinfectant or a first decontaminant. The first set of test parameters comprises a first period of time defining exposure duration of the test surface to the at least one of the first disinfectant or the first decontaminant provided in the first aerosol mist. Dispensing the first aerosol mist forms a first deposit of the at least one of the first disinfectant or the first decontaminant on the test surface of the first sample. In some embodiments, the first sample is maintained at a temperature ranging from about 65° F. to about 75° F. during dispensing of the first aerosol mist onto the test surface of the first sample. The method proceed with removing the first deposit from the test surface of the first sample and testing the first sample for one or more properties to determine effect of aerosol exposure onto the first sample. In some embodiments, removing the first deposit of the material from the test surface of the sample comprises rinsing the test surface with a solvent and drying the test surface. Examples of the one or more properties include surface corrosion, weight change, hydrogen embrittlement, cadmium removal, tensile strength, hardness, stress crazing, hardness, elasticity, sealant shear strength, and voltage withstand.

In some embodiments, the method also involves determining the first period of time defining exposure duration of the test surface to the at least one of the first disinfectant or the first decontaminant provided in the first aerosol mist. The first period of time is determined based on the composition of the at least one of the first disinfectant or the first decontaminant provided in the first aerosol. In some embodiments, other factors may be used for determining the first period of time, such as the concentration of the at least one of the first disinfectant or the first decontaminant, materials of the first samples, and the like.

In some embodiments, the method also involves, prior to testing the first sample for the one or more properties, dispensing a second aerosol mist onto the test surface of the first sample. The second aerosol mist comprises at least one of a second disinfectant or a second decontaminant. In some embodiments, the composition of the second aerosol may be the same as the composition of the first aerosol. Alternatively, the composition of the second aerosol may be different than the composition of the first aerosol. For example, a different decontaminant or a different disinfectant may be used in the second aerosol. In some embodiments, the concentration of a decontaminant or disinfectant may be different in the second aerosol than in the first aerosol. Furthermore, the second aerosol may be dispensed using the same test parameters as the first aerosol. Alternatively, the second aerosol may be dispensed using different process conditions that the first aerosol. In some embodiments, the second aerosol mist is dispensed without prior removing the first deposit of the at least one of the first disinfectant or the first decontaminant from the test surface of the first sample.

In some embodiments, the method involves, after dispensing the aerosol mist onto the test surface of the first sample and prior to removing the first deposit from the test surface of the first sample, maintaining the first deposit on the test surface of the first sample for a second period of time. During the second period of time, no aerosol mist is dispensed onto the sample. The remaining mist may be removed from the environment by recirculating air or other means. The first sample may be maintained at the same temperature during the first period of time and the second period of time.

In some embodiments, the method also involves dispensing a second aerosol mist onto a test surface of a second sample using a second set of test parameters. Dispensing the second aerosol mist forms a second deposit of at least one of a second disinfectant or a second decontaminant on the test surface of the second sample. The method may proceed with removing the second deposit from the test surface of the second sample and, after removing the second deposit, testing the second sample for the one or more properties to determine effect of aerosol exposure onto the second sample. In some embodiments, dispensing the second aerosol mist onto the test surface of the second sample and dispensing the first aerosol mist onto the test surface of the first sample are performed at the same time and, more specifically, in the same processing chamber. For example, the first sample and the second sample may be present in the same processing chamber at the same time. In this case, the second set of test parameters may be the same as the first set of test parameters. Alternatively, the second sample may be tested after testing the first sample. In this case, the method may involve determining the second set of test parameters based on testing of the first sample. More specifically, the second set of test parameters may be determined based the effect of aerosol exposure onto the first sample using the first set of test parameters. In some embodiments, the second set of test parameters varies from the first set of test parameters in at least one of a spray pattern, a droplet size, a dispensed volume, a viscosity, or a temperature of the material.

In some embodiments, the method also involves cleaning the test surface of the first sample prior to dispensing the first aerosol mist onto the test surface of the first sample. For example, a contamination may be removed from the test surface. In some embodiments, the method may involve applying a barrier onto a portion adjacent to the test surface of the first sample. The barrier protects this portion from the aerosol mist thereby preventing exposure of the portion to the mist.

In some embodiments, the test surface is positioned substantially parallel to a flow direction of the first aerosol mist while dispensing the first aerosol mist onto the test surface of the first sample. This orientation of the test surface prevents damage to the test surface from the velocity of the particles in the aerosol mist. The first aerosol mist may have a droplet size of between about 0.5 micrometers and 20 micrometers. In some embodiments, the test surface is positioned at an angle ranging from about 15° to about 30° from a direction of the gravity during dispensing of the first aerosol mist onto the test surface of the first sample.

In some embodiments, the first aerosol mist comprises a solvent. Examples of the solvent include ethanol and water. In some embodiments, the concentration of the at least one of the first disinfectant or the first decontaminant in a liquid forming the first aerosol mist is between about 1% and 10%. Some examples of the first disinfectant or the first decontaminant include hydrogen peroxide, quaternary ammonium, parachlorometaxylenol, acetic acid, and peracetic acid.

These and other embodiments are described further below with reference to the figures.

BRIEF DESCRIPTION OF THE DRAWINGS

Figure 2:
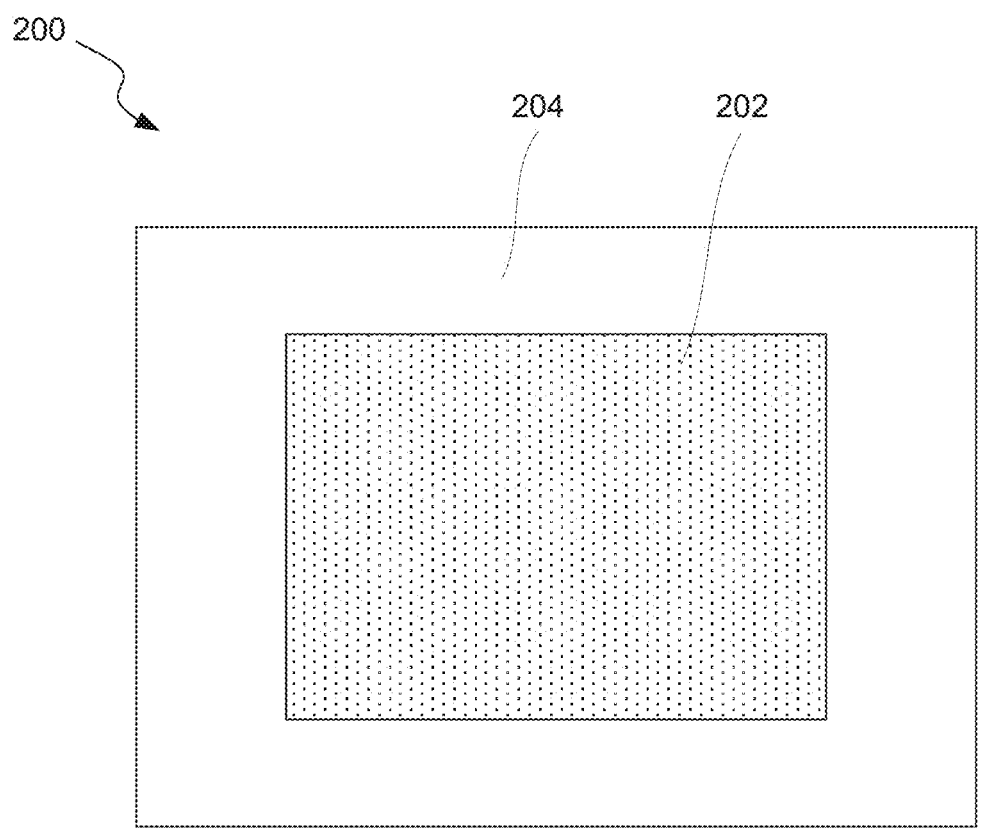

Having thus described examples of the disclosure in general terms, reference will now be made to the accompanying drawings, which are not necessarily drawn to scale, and wherein like reference characters designate the same or similar parts throughout the several views, and wherein:

Figure 1:
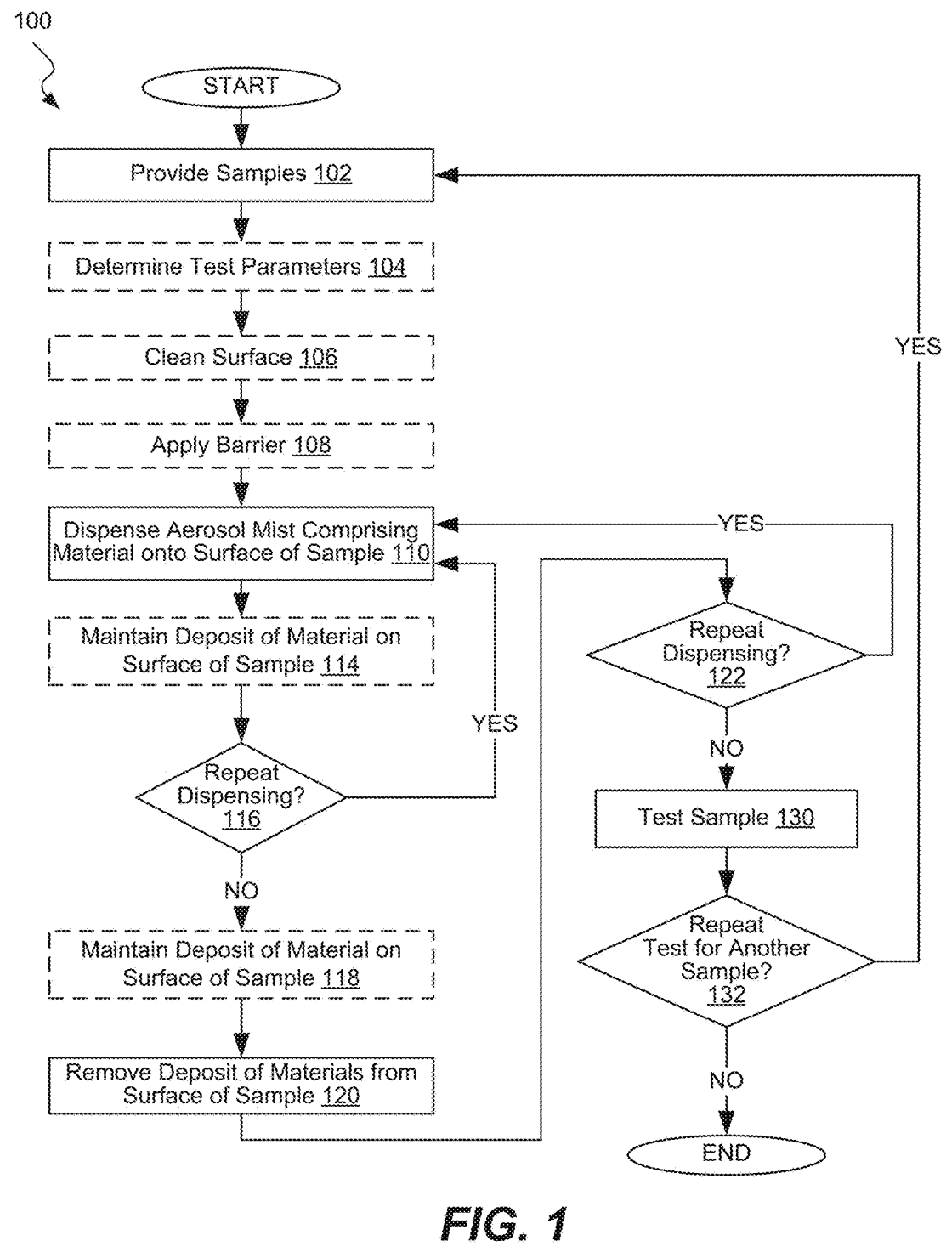

FIG. 1 is a process flowchart corresponding to a method for testing aerosol material compatibility, in accordance with some embodiments.

FIG. 2 is a schematic illustration of a sample having a test surface surrounded by a protected surface, in accordance with some embodiments.

Figure 3:
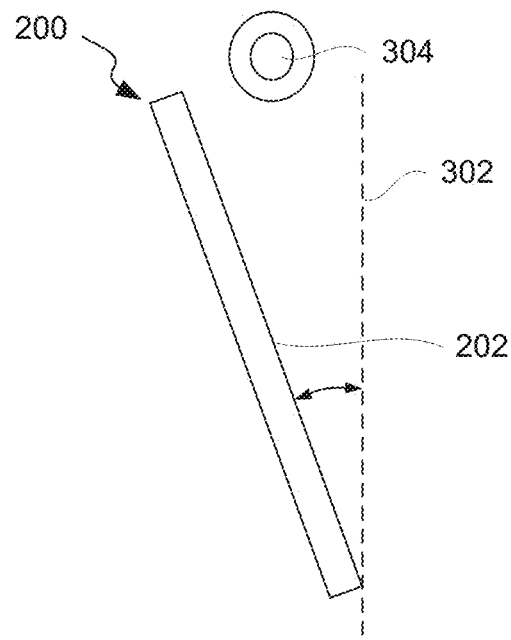

FIG. 3 illustrates a schematic side view of a sample relative to a spray nozzle used to deliver an aerosol mist to the sample, in accordance with some embodiments.

Figure 4:
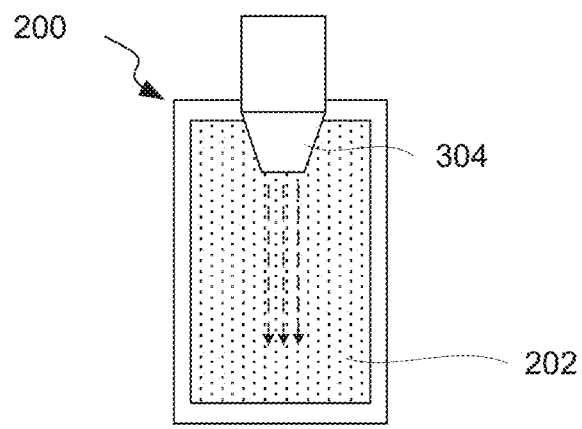

FIG. 4 illustrates a schematic top view of the sample relative to the spray nozzle, also shown in FIG. 3, in accordance with some embodiments.

Figure 5:
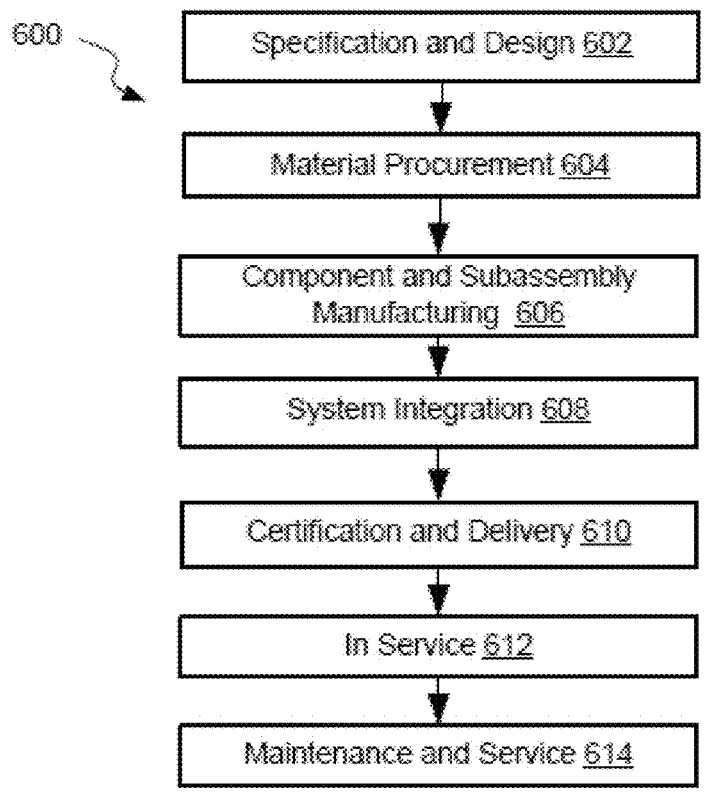

FIG. 5 is a process flowchart reflecting key operations in aircraft manufacturing and service, in accordance with some embodiments.

Figure 6:
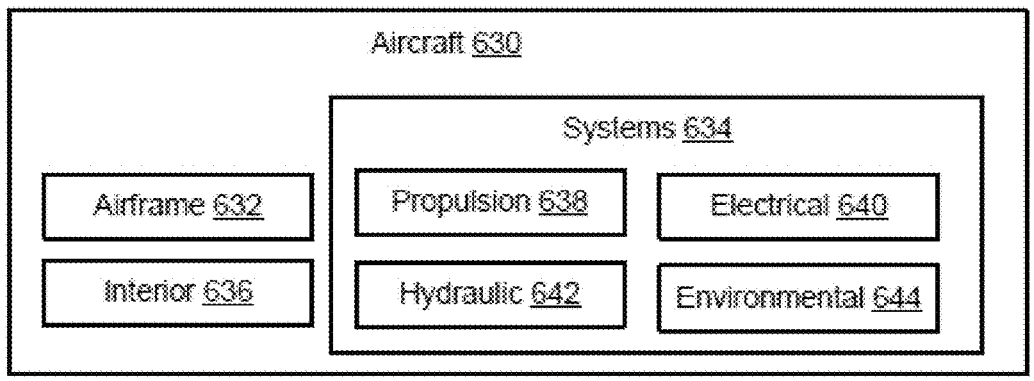

FIG. 6 is a block diagram illustrating various key components of an aircraft, in accordance with some embodiments.

DETAILED DESCRIPTION

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific examples, it will be understood that these examples are not intended to be limiting.

Reference herein to "one example" or "one aspect" means that one or more feature, structure, or characteristic described in connection with the example or aspect is included in at least one implementation. The phrase "one example" or "one aspect" in various places in the specification may or may not be referring to the same example or aspect.

Methods described herein may be used for evaluating compatibility of different materials with aerosolized disinfectants, decontaminates, and other such products. Aerosol material compatibility protocols (AMCP) may be developed based on these methods for repeatable and consistent testing of materials. The methods are based on exposing test surfaces of samples to an aerosolized mist by setting and controlling various test parameters, such as spray pattern, droplet size, dispersed volume, viscosity, temperature, and exposure duration. These test parameters may be reflective of actual operating conditions or represent accelerated testing. Furthermore, testing may be repeated using different test parameters in order to determine exposure limits, such as exposure durations, concentrations of various materials in the aerosol mist, and other factors.

Aerosolized applications of active ingredients feature low exposure times, minimal volumes dispersed, and infrequent use. These features are different from other decontamination techniques and testing methods, such as, immersion. For example, some aerosolized disinfectants have exposure time of only a few minutes, e.g., 5 minutes or 10 minutes. While aerosol can reach to various hidden surfaces, it is also capable of quick evaporation and removal from the environment by, for example, ventilation. The proposed test methods allow more precise simulation of the actual use of aerosolized materials, evaluation of actual impacts of these materials on various surfaces, reduction of correlation discrepancies associated with the conventional material compatibility methods (e.g., immersion), and various other benefits.

An aerosol is a colloid of fine solid particles or liquid droplets in air or another gas. Since most materials described herein fall into the liquid category, the references are made to droplets. However, solid particles or various combinations of solid particles and liquid droplets are also within the scope of this disclosure. The droplets may include various materials. At least one of these materials is an active ingredient capable of disinfecting bacterial and microbial contamination that these droplets may come in contact with. In some embodiments, multiple active ingredients may be provided in the same liquid forming an aerosol mist. When the droplets accumulate on a test surface, these droplets may be referred to as a deposit.

FIG. 1 illustrates a process flowchart corresponding to method 100 for testing aerosol material compatibility, in accordance with some embodiments. In general, any apparatus capable of generating an aerosol mist in a controllable manner and contain this mist and samples in a controlled environment can be used to execute various operations of method 100. The apparatus may include a fog chamber, liquid reservoir, a supply of compressed gas (e.g., air), one or more atomizing nozzles, sample supports, heater, and various controllers. The atomizing nozzles may have particular orientations relative to test surfaces of samples as further described below.

Method 100 may commence with providing one or more samples during operation 102. The sample may be also referred to as a test specimen or simply a specimen. The sample may be prepared in accordance with one or more standards, such as ASTM F483 "Standard Practice for Total Immersion Corrosion Test for Aircraft Maintenance Chemicals", ASTM F519 "Standard Test Method for Mechanical Hydrogen Embrittlement Evaluation of Plating/Coating Processes and Service Environments," or SAE AS4373 "Test Methods for Insulated Electric Wire." Operation 102 may involve identifying the sample type, sample dimension, quantity of samples, and other characteristics. For example, if a sample is tested for discoloration, a surface of the sample may be polished or otherwise specifically prepared. A sample tested for weight changes may be relatively thin, e.g., with a low volume to surface ratio. In some embodiments, the sample may be about 1 inch wide by about 2 inches long. A set of controlled samples (not tested or tested in a different manner) may be prepared during operation 102 as well.

The one or more samples may be either suspended or supported within the aerosol apparatus. For example, each sample may be suspended using a wax string or a coated non-reactive wire. In some embodiments, the one or more samples may be supported using a plastic tray, such as a tray used for salt fog applications. In general, a sample shall not contact any other sample or parts of the apparatus other than the support structure. Furthermore, the test surface of each sample may not be contacted or blocked. In some embodiments, multiple samples may be tested in the same apparatus and may be provided at the same time. When multiple samples are used, these samples may be referred to as a first sample, a second sample, and so on. Multiple samples may be tested at the same time or in sequence as further described below.

Each one of the one or more samples may be oriented relative to the nozzles of the apparatus such that the aerosol mist generated in later operations is flown in the direction substantially parallel to the test surface of each sample. This orientation helps to avoid direct aerosol impingement. In the same or other embodiments, the test surface of each sample is positioned at an angle of between about 15° and 30° from the vertical defined by the gravitational force during dispensing the aerosol mist onto the surface. This orientation helps to avoid pooling of the deposit on the surface or losing the deposit from the surface due to the gravitation force and flowing of the deposit from the surface. The angle may be adjusted depending on the surface tension, viscosity, and other characteristics of the one or more materials in the aerosol mist.

FIG. 3 illustrates a schematic side view of sample 200 relative to spray nozzle 304 and vertical 302. As shown, test surface 202 is positioned at an angle of between about 15° and 30° from vertical 302. Other angles may be used as well. FIG. 4 illustrates a schematic top view of sample 200 relative to spray nozzle 304. When multiple spray nozzles are used, all nozzles may have the same orientation relative to test surface 202 of sample 200.

In some embodiments, operation 102 may be repeated at least once, as illustrated in FIG. 1 by decision block 132, and additional samples may be provided for testing, e.g., a second sample, third sample, and so on. The second sample may similar to the first sample or different from the first sample. In some embodiments, the second sample may be selected based on test results received from testing the first sample. Additional details associated with decision block 132 are described below.

Method 100 may proceed with determining test parameters during operation 104. The test parameters may include size of aerosol droplets, aerosol flow speed, exposure temperature, duration of dispensing an aerosol mist, duration of post-dispensing exposure, duration of the overall exposure, cleaning parameters, and the like. In some embodiments, operation 104 may involve determining a first period of time, which may be duration of dispensing an aerosol mist, duration of post-dispensing exposure, or a combination of the two. In some embodiments, the first period of time represents duration of dispensing the aerosol mist, while the second period of time represents duration of post-dispensing exposure. Both periods of time may be determined during operation 104.

Various periods of time described above may be determined based the material of the aerosol mist and the sample. For example, a material used for virus decontamination may have a shorter first period than another material used for spore decontamination. In some embodiments, the first period of time is between about 2 minutes and 240 hours or more specifically between about 5 minutes and 168 hours or even between about 5 minutes and 24 hours or 10 minutes and 12 hours. The table below presents various examples of exposure durations for various contaminants.

TABLE

Exposure Durations for Various Contaminants

| Material | Exposure Duration Range | Example |
|---|---|---|
| Virus | 5 minutes-24 hours | 10 minutes |
| Spore | 5 minutes-168 hours | 24 hours |
| Toxic Industrial Chemicals (TICs) | 5 minutes-24 hours | 10 minutes |
| Chemical Warfare Agents (CWAs) | 5 minutes-24 hours | 10 minutes |

In some embodiments, the first period of time may also depend on a number of dispensing operations. For example, the overall testing method may involve multiple dispensing operations as illustrated in FIG. 1 by decision blocks 116 and 122, and the first period of time may represent only one of these cycles. As such, method 100 may include a second period of time corresponding to the second dispensing and so one.

In some embodiments, method 100 also involves repeating operation 104 at least once, as illustrated in FIG. 1 by decision block 132, and an additional set of test parameters may be determined for the additional sample, e.g., a second set of test parameters, a third set of test parameters, and so on. In some embodiments, determining the set of test parameters (e.g., for testing the second sample) may be based on results of testing a first sample. In some embodiments, the second set of test parameters varies from the first set of test parameters in at least one of a spray pattern, droplet size, dispensed volume, viscosity, temperature of the dispensed material, or temperature of the sample.

Method 100 may also involve cleaning the test surface of the sample during optional operation 106. The test surface is later exposed to the aerosol mist. The test surface may be cleaned from contaminants, oxidation, and other undesirable surface deposits. The cleaning promotes consistent exposure of the surface to one or more materials provided in the mist. The cleaned surface may represent the most severe and/or representative test conditions. The cleaning depends on the material of the sample. For example, metal samples may be cleaned with acetone or methyl ethyl ketone (MEK). However, certain types of surfaces, such as painted surfaces, cadmium plated surfaces, and other like surfaces may not be cleaned. As such, method 100 may proceed without performing operation 106 on these surfaces.

Method 100 may also involve applying a barrier onto a protected surface of the sample during optional operation 108. The barrier may be operable to protect the surface from exposure to the one or more materials in the aerosol mist. In some embodiments, a tape or wax barrier may be applied onto the additional surface. The protected surface may adjacent to the test surface of the sample. FIG. 2 is a schematic illustration of a sample 200 showing test surface 202, which is later exposed to the aerosol mist, surrounded by protected surface 204, which is blocked from the aerosol mist by the barrier.

Method 100 may proceed with dispensing an aerosol mist onto the surface of the sample during operation 110. The dispensing may be performed in accordance with the set of test parameters determined during operation 104 and described above. The dispensing may involve flowing the aerosol mist into the chamber containing the sample.

The aerosol mist is formed from a test liquid that may include one or more of a disinfectant, a decontaminant, or any spray fluid. These materials may be referred to active ingredients to distinguish them from other components of test liquids, such as solvents, surfactants, and the like. Some examples of active ingredients include hydrogen peroxide ($H_2O_2$), quaternary ammonium ($NR_4^+$, R being an alkyl group or an aryl group), parachlorometaxylenol (also known as 4-chloro-3,5-dimethylphenol, $ClC_6H_2(CH_3)_2OH$), acetic acid ($C_2H_4O_2$), peracetic acid ($C_2H_4O_3$), and ethanol ($C_2H_5OH$). Various solvents may be used to form test liquids, such as water and ethanol. The concentration of an active ingredient in a solvent may be between about 0.1% and 10% by weight or, more specifically, between about 0.5% and 5% by weight. It should be noted that material compatibility may be impacted by any component of the test liquid. Furthermore, various characteristics of the mist, such as droplet size, flow speed, concentration in the environment, temperature, acidity, and the like may impact material compatibility. The droplets may have an average size of between about 0.5 micrometers and 20 micrometers or, more specifically, between 1 micron and 10 microns. Larger droplets have a much higher settling speed than smaller droplets.

The sample may be maintained at a temperature ranging from about 65° F. to about 75° F. during dispensing the aerosol mist onto the surface of the sample. The sample may be heated to maintain this temperature due to evaporative cooling associated with the aerosol mist. In some embodiments, the temperature ranging from about 65° F. to about 75° F. is maintained up until the deposit is removed from the surface of the sample. The sample may be heated through the sample support and/or by heating the aerosol mist.

Dispensing the aerosol mist forms a deposit of the material on the surface of the sample. The deposit amount may be between 0.001 $g/in^2$ and 0.1 $g/in^2$ or, more specifically, 0.01 $g/in^2$ and 0.05 $g/in^2$. The deposit may remain on the test surface for a set period of time, which may be referred to as an exposure time. This period of time may include the duration of operation 110 and one or more of operations 117 and 118. It should be noted that the composition of the deposit may change during the exposure, for example, due to evaporation of the solvent from the deposit and/or interaction with the test surface of the sample. Humidity control may also be used to mitigate evaporation of the fluid. In some embodiments, an additional deposit is added to the surface as shown in FIG. 1 by decision block 116. More specifically, the additional deposit is added without removing the initial deposit. This process may be repeated multiple times. Each new deposit may have the same composition or different composition than the original deposit.

In some embodiments, various test conditions are monitored during operation 110. For example, atomization and density of spray may be determined by utilizing fog collectors. One such collector may be placed near the spray nozzle, while another is to be placed as far away as possible from the nozzle. Each collector shall feature a specified horizontal collecting area.

Method 100 may involve maintaining the deposit of the material on the surface of the sample during optional operation 114 and optional operation 118. For clarity, operation 114 or operation 118 is performed after operation 110 but before operation 120, i.e., after dispensing the aerosol mist onto the surface of the sample but prior to removing the deposit of the material from the surface of the sample. The deposit may be maintained for a period of time described above, which may be referred to a second period of time in order to distinguish it from other periods of time, such as dispensing. The second period of time may be a subset of the first period of time or a subsequent period of time described above.

In some embodiments, operation 110 may be repeated for the same sample multiple times without any intermediate operation 114. In this case, multiple deposits may be maintained on the surface of the sample during operation 118. Alternatively, operation 110 may follow by operation 114 prior to repeating operation 110. As such, a break in dispensing may be presented in between two consecutive dispensing operations. Still, multiple deposits may be maintained on the surface of the substrate during operation 118 in addition to operations 114.

Method 100 may proceed with removing the deposit of the material from the test surface of the sample during operation 120. This removing operation may involve rinsing the surface with a solvent and drying the surface. The solvent may be suitable to dissolve the deposit, which may be at least partially dried on the surface at the beginning of operation 120. The solvent may be the same as the solvent used for the aerosol mist or different, e.g., if the solvent may have an impact on the material compatibility. In some embodiments, the temperature of the rinsing solution may be less than 100° F. to avoid additional impact from operation 120.

Method 100 may proceed with testing the sample for one or more properties to evaluate effect of aerosol exposure onto the sample during operation 130. Operation 130 may be performed after operation 120 to avoid effects of remaining materials on the surface of the substrate. Some examples of the test properties include surface corrosion, weight change, hydrogen embrittlement, cadmium removal, tensile strength, hardness, stress crazing, hardness, elasticity, sealant shear strength, and voltage withstand. Operation 130 may be performed in accordance with one or more standard tests, such as ASTM F483 "Standard Practice for Total Immersion Corrosion Test for Aircraft Maintenance Chemicals," ASTM F519 "Standard Test Method for Mechanical Hydrogen Embrittlement Evaluation of Plating/Coating Processes and Service Environments," ASTM D471 "Standard Test Method for Rubber Property—Effect of Liquids," ASTM D2240 "Standard Test Method for Rubber Property—Durometer Hardness," ASTM F484 "Standard Test Method for Stress Crazing of Acrylic Plastics in Contact with Liquid or Semi-Liquid Compounds," ASTM F502 "Standard Test Method for Effects of Cleaning and Chemical Maintenance Materials on Painted Aircraft Surfaces," ASTM D3039 "Standard Test Method for Tensile Properties of Polymer Matrix Composite Materials," ASTM D1002 "Standard Test Method for Apparent Shear Strength of Single-Lap-Joint Adhesively Bonded Metal Specimens by Tension Loading (Metal-to-Metal)," SAE MA4872 "Paint Stripping of Commercial Aircraft—Evaluation of Materials and Process," SAE AS4373 "Test Methods for Insulated Electric Wire."

In some embodiments, method 100 also involves repeating dispensing the aerosol mist onto the surface of the same sample as shown in FIG. 1 by decision blocks 116 and 122. This second dispensing may be performed prior to testing the sample for the one or more properties. Furthermore, the second dispensing is performed prior to removing the deposit of the material from the surface of the sample, i.e., the deposit formed during the first dispensing, as shown by decision block 116. In other words, dispensing the aerosol mist may be repeated without prior removing the deposit of the material from the surface of the sample. Alternatively, the deposit of the material may be removed prior to repeating dispensing the aerosol mist onto the surface of the sample as shown in FIG. 1 by decision block 122.

In some embodiments, method 100 may involve dispensing the aerosol mist onto a surface of another sample, e.g., a second sample, as shown in FIG. 1 by decision block 132. In general, dispensing may be performed for multiple additional samples either at the same time (e.g., multiple samples in the same aerosol dispensing chamber) or sequentially (e.g., a second sample tested after completing the testing of the previous sample). Multiple samples may be made from the same material and/or have the same dimensions. In some embodiments, different samples may be used. For example, samples made from different materials may be tested in parallel in the same chamber. Furthermore, the same or different test parameters may be used for testing different samples. For example, a first sample may be tested using a first set of test parameters, while a second sample may be tested using a second set of test parameters that is different from the first set of test parameters. Different sets of test parameters may have different dispensing durations, post-dispensing exposure durations, different sample temperatures, and other differences in test parameters.

An aircraft manufacturing and service method 600 shown in FIG. 5 and an aircraft 630 shown in FIG. 6 will now be described to better illustrate various features of processes and systems presented herein. During pre-production, aircraft manufacturing and service method 600 may include specification and design 602 of aircraft 630 and material procurement 604. The production phase involves component and subassembly manufacturing 606 and system integration 608 of aircraft 630. Thereafter, aircraft 630 may go through certification and delivery 610 in order to be placed in service 612. While in service by a customer, aircraft 630 is scheduled for routine maintenance and service 614 (which may also include modification, reconfiguration, refurbishment, and so on). While the embodiments described herein relate generally to servicing of commercial aircraft, they may be practiced at other stages of the aircraft manufacturing and service method 600.

Each of the processes of aircraft manufacturing and service method 600 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

As shown in FIG. 6, aircraft 630 produced by aircraft manufacturing and service method 600 may include airframe 632, interior 636, and multiple systems 634 and interior 636. Examples of systems 634 include one or more of propulsion system 638, electrical system 640, hydraulic system 642, and environmental system 644. Any number of other systems may be included in this example. Although an aircraft example is shown, the principles of the disclosure may be applied to other industries, such as the automotive industry.

Apparatus and methods embodied herein may be employed during any one or more of the stages of aircraft manufacturing and service method 600. For example, without limitation, components or subassemblies corresponding to component and subassembly manufacturing 606 may be fabricated or manufactured in a manner similar to components or subassemblies produced while aircraft 630 is in service.

Also, one or more apparatus embodiments, method embodiments, or a combination thereof may be utilized during component and subassembly manufacturing 606 and system integration 608, for example, without limitation, by substantially expediting assembly of or reducing the cost of aircraft 630. Similarly, one or more of apparatus embodiments, method embodiments, or a combination thereof may be utilized while aircraft 630 is in service, for example, without limitation, to maintenance and service 614 may be used during system integration 608 and/or maintenance and service 614 to determine whether parts may be connected and/or mated to each other.

Different examples and aspects of the apparatus and methods are disclosed herein that include a variety of components, features, and functionality. It should be understood that the various examples and aspects of the apparatus and methods disclosed herein may include any of the components, features, and functionality of any of the other examples and aspects of the apparatus and methods disclosed herein in any combination, and all of such possibilities are intended to be within the spirit and scope of the present disclosure.

Many modifications and other examples of the disclosure set forth herein will come to mind to one skilled in the art to which the disclosure pertains having the benefit of the teachings presented in the foregoing descriptions and the associated drawings.

Therefore, it is to be understood that the disclosure is not to be limited to the specific examples presented and that modifications and other examples and aspects are intended to be included within the scope of the appended claims.

Moreover, although the foregoing descriptions and the associated drawings describe example embodiments in the context of certain illustrative combinations of elements and/or functions, it should be appreciated that different combinations of elements and/or functions may be provided by alternative implementations without departing from the scope of the appended claims.

What is claimed is:

1. A method for testing aerosol material compatibility, the method comprising:
dispensing a first aerosol mist onto a test surface of a first sample using a first set of test parameters,
wherein the first aerosol mist comprises at least one of a first disinfectant or a first decontaminant,
wherein the first set of test parameters comprises a first period of time defining exposure duration of the test surface to the at least one of the first disinfectant or the first decontaminant provided in the first aerosol mist,
wherein the first set of test parameters further comprises a parameter selected from the group consisting of spay duration of the first disinfectant or the first decontaminant, a spray pattern of the at least one of the first disinfectant or the first decontaminant, a droplet size of the first aerosol mist formed by the at least one of the first disinfectant or the first decontaminant, a dispensed volume of the at least one of the first disinfectant or the first decontaminant, a viscosity of the at least one of the first disinfectant or the first decontaminant, a temperature of the test surface of the first sample, and a temperature of the at least one of the first disinfectant or the first decontaminant, and
wherein dispensing the first aerosol mist forms a first deposit of the at least one of the first disinfectant or the first decontaminant on the test surface of the first sample;
removing the first deposit from the test surface of the first sample;
testing the first sample for one or more properties to determine effect of aerosol exposure onto the first sample; and
monitoring atomization and density of the first aerosol mist using one or more fog collectors.

2. The method of claim 1, wherein the one or more properties are selected from the group consisting of weight change, hydrogen embrittlement, cadmium removal, tensile strength, hardness, stress crazing, hardness, elasticity, sealant shear strength, and voltage withstand.

3. The method of claim 1, further comprising determining the first period of time,
wherein the first period of time is determined based on composition of the at least one of the first disinfectant or the first decontaminant provided in the first aerosol mist.

4. The method of claim 1, wherein dispensing the first aerosol mist onto the test surface of the first sample is performed using multiple spray nozzles and wherein all of the multiple spray nozzles have same orientation relative to the test surface of the first sample.

5. The method of claim 1, further comprising, prior to testing the first sample for the one or more properties, dispensing a second aerosol mist onto the test surface of the first sample using a second set of test parameters, wherein the second aerosol mist comprises at least one of a second disinfectant or a second decontaminant.

6. The method of claim 5, wherein the second aerosol mist is dispensed without prior removing the first deposit of the at least one of the first disinfectant or the first decontaminant from the test surface of the first sample.

7. The method of claim 5, wherein the second aerosol mist has a different composition than the first aerosol mist.

8. The method of claim 5, wherein the second set of test parameters is different from the first set of test parameters.

9. The method of claim 1, further comprising dispensing a second aerosol mist onto a test surface of a second sample using a second set of test parameters,
wherein dispensing the second aerosol mist forms a second deposit of at least one of a second disinfectant or a second decontaminant on the test surface of the second sample;
removing the second deposit from the test surface of the second sample; and
after removing the second deposit, testing the second sample for the one or more properties to determine effect of aerosol exposure onto the second sample.

10. The method of claim 9, wherein the second set of test parameters varies from the first set of test parameters.

11. The method of claim 1, wherein the at least one of the first disinfectant or the first decontaminant comprises an active ingredient selected from the group consisting of hydrogen peroxide ($H_2O_2$), quaternary ammonium, parachlorometaxylenol (also known as 4-chloro-3,5-dimethylphenol, $ClC_6H_2(CH_3)_2OH$), acetic acid ($C_2H_4O_2$), peracetic acid ($C_2H_4O_3$), and ethanol ($C_2H_5OH$).

12. The method of claim 11, wherein the at least one of the first disinfectant or the first decontaminant comprises a solvent selected from the group consisting of water and ethanol.

13. The method of claim 12, wherein a concentration of the active ingredient in the at least one of the first disinfectant or the first decontaminant is between about 0.1% and 10% by weight.

14. The method of claim 1, wherein the first aerosol mist has a droplet size of between about 0.5 micrometers and 20 micrometers.

15. A method for testing aerosol material compatibility, the method comprising:
dispensing a first aerosol mist onto a test surface of a first sample using a first set of test parameters,
wherein the first aerosol mist comprises at least one of a first disinfectant or a first decontaminant,
wherein the first set of test parameters comprises a first period of time defining exposure duration of the test surface to the at least one of the first disinfectant or the first decontaminant provided in the first aerosol mist,
wherein the first set of test parameters further comprises a parameter selected from the group consisting of spay duration of the first disinfectant or the first decontaminant, a spray pattern of the at least one of the first disinfectant or the first decontaminant, a droplet size of the first aerosol mist formed by the at least one of the first disinfectant or the first decontaminant, a dispensed volume of the at least one of the first disinfectant or the first decontaminant, a viscosity of the at least one of the first disinfectant or the first decontaminant, a temperature of the test surface of the first sample, and a temperature of the at least one of the first disinfectant or the first decontaminant, and wherein dispensing the first aerosol mist forms a first deposit of the at least one of the first disinfectant or the first decontaminant on the test surface of the first sample;
removing the first deposit from the test surface of the first sample;
testing the first sample for one or more properties to determine effect of aerosol exposure onto the first sample;
dispensing a second aerosol mist onto a test surface of a second sample using a second set of test parameters,
wherein dispensing the second aerosol mist forms a second deposit of at least one of a second disinfectant or a second decontaminant on the test surface of the second sample;
removing the second deposit from the test surface of the second sample;
after removing the second deposit, testing the second sample for the one or more properties to determine effect of aerosol exposure onto the second sample; and determining the second set of test parameters,
wherein the second set of test parameters is determined based the effect of aerosol exposure onto the first sample using the first set of test parameters.

16. The method of claim 1, further comprising cleaning the test surface of the first sample prior to dispensing the first aerosol mist onto the test surface of the first sample.

17. The method of claim 1, further comprising applying a barrier onto a portion adjacent to the test surface of the first sample.

18. The method of claim 1, wherein the first sample is maintained at a temperature ranging from about 65° F. to about 75° F. during dispensing of the first aerosol mist onto the test surface of the first sample.

19. The method of claim 15, further comprising monitoring atomization and density of the first aerosol mist using one or more fog collectors.

20. The method of claim 1, wherein the first sample is an interior component of an aircraft.

* * * * *